United States Patent [19]
Takahashi

[11] Patent Number: 5,503,831
[45] Date of Patent: Apr. 2, 1996

[54] LIPASE INHIBITOR DERIVED FROM A DEFATTED RICE GERM

[75] Inventor: Hidehiko Takahashi, Tokyo, Japan

[73] Assignee: Yakurigaku Chuo Kenkyusho, Tokyo, Japan

[21] Appl. No.: 249,295

[22] Filed: May 25, 1994

[30] Foreign Application Priority Data

Jun. 25, 1993 [JP] Japan ................................. 5-155194

[51] Int. Cl.⁶ ............................................... A61K 35/78
[52] U.S. Cl. ................... 424/195.1; 426/648; 426/655; 514/905
[58] Field of Search ................... 424/195.1; 426/648, 426/655, 805; 514/909

[56] References Cited

U.S. PATENT DOCUMENTS 4,056,637  11/1977  Hagiwara et al. .................... 426/52

FOREIGN PATENT DOCUMENTS

| | | |
|---|---|---|
| 0575846 | 12/1993 | European Pat. Off. . |
| 4040874 | 6/1991 | Germany . |
| 3-284627 | 12/1991 | Japan . |
| 4-300839 | 10/1992 | Japan . |

OTHER PUBLICATIONS

JP-A-4 327–536 (AN 92–430058) (Kyodo Nugyo KK) Derwent Publications Ltd., London, GB; 17 November 1992, Abstract.

JP-A-01 034 264—Patent Abstracts of Japan—vol. 013, No. 221, May 23, 1989, (Yakurigaku Chuo Kenkyusho KK).

JP-A-1 075430 (AN 89–132551) (Tamanoisu KK) Derwent Publications, Ltd., London, GB; 22 Mar. 1989, Abstract.

KR-A-9 203 054 (AN 93–033769) (Nongsim Co.) Derwent Publications Ltd., London, GB; 13 Apr. 1992, Abstract.

JP-4300839—Patent Abstracts of Japan—vol. 17, No. 119, Dec. 3, 1993 (Nisshin Flour Milling Co. Ltd.).

JP-4279529—Patent Abstracts of Japan—vol. 17, No. 79, Feb. 17, 1993 (Gekkeikan Sake Co. Ltd.).

Arg. Biol. Chem., 38(1), 97–101, 19974.

Arg. Biol. Chem., 40(5), 889–897, 1976.

Gastroenterology, vol. 75, No. 3, pp. 382–386, 1978.

J. Clin. Invest., vol. 64, Nov. 1979, pp. 1303–1308.

Journal of Lipid Research, vol. 25, pp. 1214–1221, 1984.

The Journal of Biological Chemistry, vol. 260, No. 4, Issue of Feb. 25, 1985, pp. 2268–2273

*Primary Examiner*—John W. Rollins
*Attorney, Agent, or Firm*—Armstrong, Westerman, Hattori, McLeland & Naughton

[57] ABSTRACT

A composition having lipase inhibiting activity is prepared by extracting defatted rice germ with water at room temperature. That composition, which is useful in preventing or treating obesity, can be incorporated into food products.

7 Claims, 1 Drawing Sheet

LIPASE INHIBITOR DERIVED FROM A DEFATTED RICE GERM

BACKGROUND OF THE INVENTION

1. Field of the Invention

The present invention relates to a crude lipase inhibitor-containing product, its purified preparations, anti-obesity foods and anti-obesity feeds for pets which are useful for preventing or treating obesity which induces so-called adult diseases such as cardiac disease, arteriosclerosis, diabetes and the like.

People often suffer from obesity by eating meals containing high amounts of fats and oils. In this connection, the rate of occurance of the above adult diseases is gradually increasing in parallel with the degree of obesity. For treatment of such a trend, there should be a way to disturb digestion and absorption of fats and oils, in addition to improvement of diet to low fat and low oil Japanese type foods.

2. Description of the Prior Art

As an inhibitive substance of lipase, for example, Patent Kokai 4-300839 reports that serum albumin, β-lactoglobulin or a certain kind of soy-bean protein or basic protein derived from wheat-germ will inhibit the action of lipase, thereby suppressing or inhibiting decomposition of emulsified lipids.

However, among the above mentioned materials, serum albumin, β-lactoglobulin or a certain soy-bean protein does not exert such an action in the presence of bile acids.

On the contrary, there is reported that the basic protein derived from wheat germ suppresses or inhibits action of lipid-decomposition enzyme even in an emulsified system of lipids in the presence of sodium taurocholic acid which is a bile acid.

SUMMARY OF THE INVENTION

It is an object of the present invention to provide a crude product containing a lipase inhibitor derived from a defatted rice germ, and also a lipase-inhibitor preparation obtained by partially purifying said crude product. It is a further object of the present invention to provide anti-obesity foods and feeds having incorporated therein said crude lipase-inhibitor product or said preparation.

Referring to lipid-decomposition enzyme inhibitor materials, which are derived from rice germ in the present invention, a water-soluble protein (water-soluble extract) resulting from rice germ can be obtained by defatting the rice germ, which is followed by water-extraction. Said materials may exert inhibiting or suppressing effect on lipase in the presence of a bile acid and in a lipid-emulsified system. The present inventor has found that in such a function and effect the present lipase inhibitor derived from rice germ is conspicuously remarkable, as compared with already known analogous materials resulting from wheat germ, soy bean, etc.

DESCRIPTION OF PREFERRED EMBODIMENT OF THE INVENTION

Figure 1:
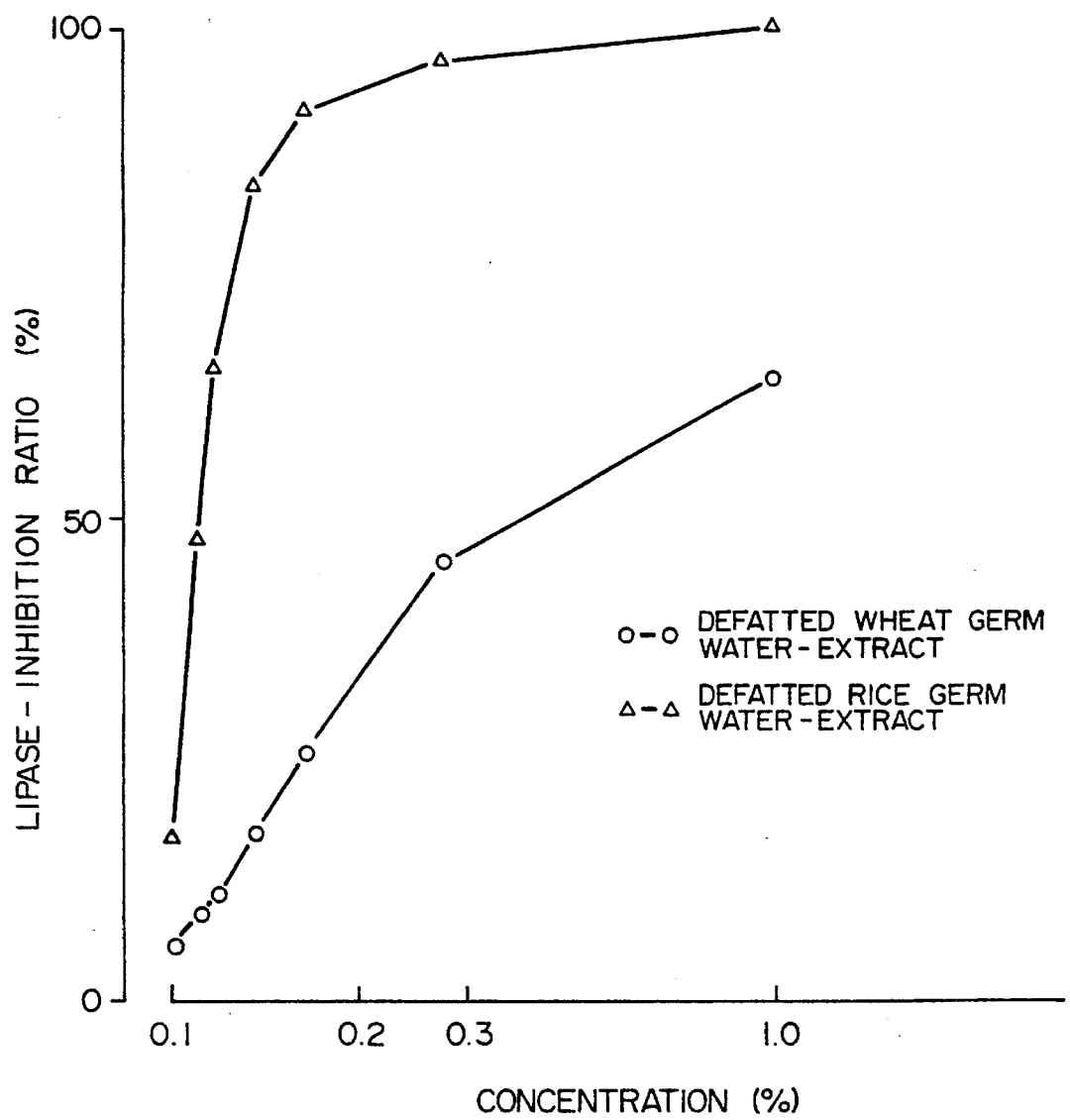
FIG. 1 is the drawing showing in a semi-logarithmic graph a comparison between rice germ water-extract of the present invention and wheat germ water-extract of the prior art, in respect to lipase-inhibitor activity.

For better understanding of the present invention, the present invention will be specifically explained relying on the following examples but is not limited thereto. This means that any kind or state of water-extracts obtained from a defatted rice germ may be used as a lipid-decomposition enzyme inhibitor material.

Defatting method of rice germ

By using a super-critical carbon dioxide or n-hexane, oil-soluble fraction was separated (i.e. defatted) from rice germ, which was before hand applied with crushing or pressure as a pretreatment. The present inventor designated the thus-obtained lipase inhibitor derived from the defatted rice germ as "Defattogen".

EXAMPLE 1

(1) Defatting of rice germ with n-hexane 350.0 g of rice germ was crushed as a pretreatment, stirred in 3 liters of n-hexane at room temperature for 3 hrs., and then filtered. The filtrate was further stirred in 2 liters of n-hexane at room temperature for 1.5 hrs., and then filtered. The resulting residue was dried at 40° C. for 2 hrs., and thereafter dried in a desiccator under a reduced pressure for 10 hrs. to obtain a defatted substance with a yield of 65.4%. On the other hand, the total filtrate was concentrated under a reduced pressure to obtain an oil portion of rice germ oil with a yield of 21.3%.

(2) Defatting of rice germ by means of super critical carbon dioxide (SCE)

126.2 g of rice germ was separated into a defatted substance and an oil portion under such conditions as 350 kgf/cm$^2$/40° C. of extraction pressure, 60 kgf/cm$^2$/40° C. of separation pressure, 10N liters/min. of $CO_2$ flow-rate and 58 of extracting agent rate. As a result, the obtained defatted product was 91.38 g with yield of 72.4%, and the oil portion was 30.38 g with yield of 24.1%.

Preparation example of water-soluble protein derived from rice germ

The rice germ defatted by the above treatment method (1) or (2) was applied to (i) water-extraction to obtain a water-soluble fraction and then to step (ii) dialysis or step (iii) ultrafiltration, and further to freeze-drying to obtain powder containing a crude water-soluble protein. In order to conduct the dialysis of step (ii), a cellulose tube for use of dialysis (fractional molecular weight of 14,000) (manufactured by VISKASE CO., LTD.) and in order to conduct ultra filtration of step (iii), a hollow filament-type ultrafiltration module (fractional molecular weight of 30,000) FB 02 (0.25 m$^2$) FUS 0382 (manufactured by Daicel K.K.) can be used respectively.

EXAMPLE 2

To 25.0 g of rice germ an amount of ten times of water was added. This was stirred at room temperature for 6 hrs. and then centrifuged in 3000 r.p.m. for 20 min. Its supernatant solution was lyophilized to obtain powder with yield of 30.8%. Protein content of the obtained powder was 27.0% in terms of albumin in accordance with Cu-Folin method.

As to the obtained lyophilized product of defatted rice germ water-extract, ion-exchange chromatography, gel-filtration chromatography and reversed phase chromatography were sequentially conducted to separate highly active components inhibiting a lipase into the three kinds of bands of 54K, 38K and 27.5K. As the result of analysis of N-terminal amino acids sequence of each band, said three kinds of bands were all consistent with each other.

Said N-terminal amino acids sequence are shown as follows:

RDRRGEGSSEEED?GR

With reference to the existence of the three kinds of bands, the following presumption was made:

They are composed of the same polypeptide chain, but are different in manner of being modified with sacchrides.

They are different in the lengths of peptides on c-terminal side.

The above obtained sequence of amino acids is a novel sequence which has not been known yet since none conforming to any protein data base exists.

EXAMPLE 3

Further, 120 ml of the above supernatant solution was applied to dialysis at room temperature for 4 hrs. with 3 liters of pure water/hr. of dialysis speed to concentrate to molecular weight of 14,000 or more. As the result, powder having 49.5% of protein content was obtained with yield of 13.6%.

EXAMPLE 4

To 250 g of rice germ, which was CES-defatted after having been pressed as a pretreatment, 20 times an amount of water was added and then stirred at room temperature for 6 hrs. Thereafter, it was centrifuged at 8000 r.p.m. for 20 min. and then, the resulting supernatant was concentrated by ultrafiltration to molecular weight of 30,000 or more. As a result of the similar treatment to the above, powder having protein content of 49.5% was obtained with yield of 10.5%. Determination of inhibitory action to lipase activity by water-soluble protein This determination was conducted by using lipase-determination reagent (manufactured by Boehringer Manheim A. G.) and taking adsorbance at wave-length of 365 nm as an index. When an activity of lipase decomposing a lipid triolein is assumed to be 100, inhibition ratio (%) of a sample is indicated with how much the sample lowers the decomposition of a lipid triolein by lipase.

EXAMPLE 5

0.5 ml of aqueous sample in each concentration and 0.1 ml of a lipase solution (lipase: 0.044 U; 37° C.) were pre-incubated at 37° C. for 5 min. and 2.0 ml of *) substrate solution (containing triolein) was added thereto. At 365 nm of wave-length, adsorbance of the resulting solution was determined after 4 min. and 14 min. to as certain the decrease of absorbance accompanying the substrate decomposition reaction by lipase.

*) Final composition and concentration of the reaction solution: triolein 0.30 mM, trisbuffer solution (pH 9.2) 26 mM, sodium deoxycholate 19 mM, calcium chloride 0.1 mM, colipase 3 mg/l.

As a specific example of lipase activity-inhibitory action by water-extract derived from rice germ, lipase activity inhibition ratio(%) of water-extract of sample defatted by super-critical carbon dioxide is shown in Table 1.

Table 1 shows that water-extracts derived from rice germ have an inhibitory action to lipase activity and that inhibitory ratio of lipase activity increases by exclusion of low molecular substances through dialysis, ultrafiltration etc., and also by elevation of protein content (%).

TABLE 1

Lipase-activity inhibitory ratio of water extract of rice germ defatted by super critical carbon dioxide

| Sample | Protein content (%) | Concentration of sample (%) | Lipase-activity inhibitory ratio (%) |
|---|---|---|---|
| Blank | 0 | 0 | 0 |
| [A] | | | |
| 1) Water-extract | 27.0 | 0.25 | 56.5 |
| | | 0.5 | 98.3 |
| | | 1.0 | 101.0 |
| 2) Dialysate of water-extract | 49.5 | 0.25 | 85.5 |
| | | 0.5 | 101.0 |
| | | 1.0 | 106.0 |
| [B] | | | |
| 1) Water-extract | 20.4 | 0.25 | 33.3 |
| | | 0.5 | 75.3 |
| | | 1.0 | 95.0 |
| 2) Ultra-filtered product of water-extract | 35.6 | 0.25 | 74.7 |
| | | 0.5 | 96.3 |
| | | 1.0 | 101.0 |

Foot note) [A]: Sample was crushed as pretreatment for defatting.
[B]: Sample was pressed as pretreatment for defatting.

EXAMPLE 6

The following experiments were conducted to investigate properties of lipase inhibitor contained in a defatted rice germ. As the result, there were obtained data sufficient to suggest the fact that the entity of lipase inhibitor is a protein:

1) When water-extract of defatted rice germ was applied to a heat-treatment at 85° C. for 60 min., the lipase inhibitor was deactivated as much as about 30–35%.
2) When incubated at 37° C. for 4 hrs. together with Pronase E, the water-extract was almost all deactivated.

EXAMPLE 7

Activity in vivo of lipase inhibitor (Defattogen) contained in rice germ was investigated using rats.

That is, male Wistar rats were used. Control group (seven rats) was given a conventional breeding feed, and test group was given the feed, in which water extract of rice germ defatted by super critical extraction method was incorporated in an amount of 10% by weight.

The Wistar rats were allowed to freely take the feeds and water for the experimental period of two weeks.

Prior to the start of the experiment and after the completion thereof, determination of body weights and blood gathering of the test rats were conducted.

The experimental results were summarized in Table 2. As shown in Table 2, Defattogen has significantly controlled ($P<0.1$) the increase of body weight, and significantly reduced ($P<0.1$) blood sugar, HbAlc, plasma total cholesterol and triglyceride levels.

TABLE 2

| | In vivo effect of Defattogen | | | | |
|---|---|---|---|---|---|
| | Increase of body weight (g) | Decrease of blood sugar | Decrease of HbAlc | Decrease of plasma total cholesterol | Decrease of plasma triglyceride |
| Control group | 100.4 ± 12.59 | 9.00 ± 15.16 | 0.343 ± 0.127 | −5.71 ± 8.67 (increase) | 15.86 ± 19.42 |
| Test group | 63.8 ± 6.058 | 33.6 ± 14.10 | 0.540 ± 0.124 | 9.20 ± 11.43 | 68.60 ± 26.14 |
| Synopsis | Depression of body weight change $P < 0.1\%$ | Decrease of blood sugar level $P < 0.1\%$ | Decrease of HbAlc value $P < 0.1\%$ | Decrease of plasma total cholesterol level $P < 0.1\%$ | Decrease of plasma triglyceride level $P < 0.1\%$ |

EXAMPLE 8

Comparative experiment of lipase-inhibitor activities between water extracts of a defatted wheat germ and a defatted rice germ were conducted. As the result the latter was proved to be superior to the former in the points of yield and activity (unit/g).

Defatted germ was treated in such a manner that 10 g of each sample was extracted with 200 ml of a distilled water, centrifuged and then its supernatant was lyophilized.

Yield:

Wheat germ 36.77%

Rice germ 40.66%

Lipase-inhibitor activity:

As shown in FIG. 1 (semi-logarithmic graph of extract concentration vs inhibition ratio), the rice water-extract was 4.16 times the wheat water-extract, in respect to the activity (unit/g) at about 50% inhibition ratio.

What we claim is:

1. A foodstuff having incorporated therein a composition exhibiting lipase inhibiting activity prepared by defatting rice germ, and extracting the defatted rice germ with water at room temperature.

2. A foodstuff according to claim 1, wherein the rice germ is defatted by extraction with an organic solvent.

3. A foodstuff according to claim 1, wherein the rice germ is defatted by extraction with super critical carbon dioxide.

4. A foodstuff according to claim 1, wherein the water extract of the defatted rice germ is purified by dialysis or by ultrafiltration.

5. A foodstuff according to claim 4, wherein the water extract purified by dialysis or by ultrafiltration is lyophilized.

6. A foodstuff according to claim 1, wherein the water extract of the defatted rice germ is lyophilized.

7. A composition having lipase inhibiting activity prepared by defatting rice germ, and extracting the defatted rice germ with water at room temperature.

* * * * *